United States Patent
Jain et al.

(10) Patent No.: US 11,779,545 B2
(45) Date of Patent: Oct. 10, 2023

(54) TRANSDERMAL PATCH PACKAGING FILM

(71) Applicant: AMCOR FLEXIBLES NORTH AMERICA, INC., Neenah, WI (US)

(72) Inventors: Rishabh Jain, Appleton, WI (US); Yuan Liu, Neenah, WI (US)

(73) Assignee: Amcor Flexibles North America, Inc., Neenah, WI (US)

(*) Notice: Subject to any disclaimer, the term of this patent is extended or adjusted under 35 U.S.C. 154(b) by 66 days.

(21) Appl. No.: 16/615,199

(22) PCT Filed: Jun. 14, 2017

(86) PCT No.: PCT/US2017/037464
§ 371 (c)(1),
(2) Date: Nov. 20, 2019

(87) PCT Pub. No.: WO2018/231219
PCT Pub. Date: Dec. 20, 2018

(65) Prior Publication Data
US 2020/0155473 A1    May 21, 2020

(51) Int. Cl.
| | |
|---|---|
| A61K 9/70 | (2006.01) |
| A61K 31/465 | (2006.01) |
| A61M 35/00 | (2006.01) |
| B32B 7/12 | (2006.01) |
| B32B 27/06 | (2006.01) |
| B32B 27/36 | (2006.01) |

(52) U.S. Cl.
CPC ............ *A61K 9/703* (2013.01); *A61K 31/465* (2013.01); *A61M 35/00* (2013.01); *B32B 7/12* (2013.01); *B32B 27/06* (2013.01); *B32B 27/36* (2013.01); *A61M 2209/06* (2013.01); *B32B 2307/7244* (2013.01); *B32B 2439/80* (2013.01)

(58) Field of Classification Search
None
See application file for complete search history.

(56) References Cited

U.S. PATENT DOCUMENTS

| | | | |
|---|---|---|---|
| 5,950,830 A | 9/1999 | Trigger | |
| 5,958,552 A * | 9/1999 | Fukuda | B32B 27/20 428/141 |
| 6,238,788 B1 * | 5/2001 | Bradt | B32B 27/08 156/308.2 |
| 6,905,016 B2 | 6/2005 | Kanios et al. | |
| 8,186,506 B2 | 5/2012 | Kanios et al. | |
| 2005/0136202 A1 | 6/2005 | Kendig et al. | |
| 2006/0040076 A1 | 2/2006 | Franzyshen et al. | |
| 2013/0323513 A1 * | 12/2013 | Hubbard | B32B 27/40 428/424.2 |
| 2014/0083890 A1 | 3/2014 | Ishizaki et al. | |
| 2015/0225151 A1 | 8/2015 | Osborn et al. | |
| 2019/0366694 A1 * | 12/2019 | Stell | B32B 7/10 |

FOREIGN PATENT DOCUMENTS

WO        2017034560 A1    3/2017

OTHER PUBLICATIONS

Hawkins, G., "Medical Packaging Rigid Materials Update HealthPack 2016" [PowerPoint slides]. Retrieved online Mar. 17, 2016 at https://www.innovativetechnologyconferences.com/files/Hawkins_Gary.pdf.

* cited by examiner

*Primary Examiner* — David J Blanchard
*Assistant Examiner* — Daniel F Coughlin (57) ABSTRACT

A multilayer flexible film for packaging a transdermal patch product comprising a pharmaceutical active agent comprises: a product-contacting sealing layer comprising a co-polyester having a surface energy of at least 50 dyne/cm$^2$; and one or more layers above the product-contacting sealing layer. The pharmaceutical active agent may comprise nicotine. An average adhesion force to peel the transdermal patch from the product-contacting sealing layer may be less than 100 g/inch (39.37 g/cm).

20 Claims, 3 Drawing Sheets

TRANSDERMAL PATCH PACKAGING FILM

TECHNICAL FIELD

The present disclosure relates generally to packaging suitable for packaging an article for collecting or administering a physiologically active substance such as a transdermal patch product comprising a pharmaceutical active agent.

BACKGROUND

Pharmaceuticals such as the drugs fentanyl and nicotine are often administered through the use of transdermal patches which are applied to a patient's skin to permit drug delivery over time by absorption. Prior to application of a drug containing patch, the patch is packaged in a pouch which is designed to be opened to permit access to the patch by the patient or caregiver for application to a patients skin. Suitable packaging for transdermal patches should contain the patch and its drug within the package while protecting the patch from contamination and deleterious effects from the external environment. Thus, articles such as a pouch may hold a transdermal patch to protect the patch and its drug contents from contact or exposure to unwanted materials such as microbes, insects, air, moisture, sunlight, etc. The container is typically sealed e.g. by a heat seal to provide a hermetic barrier.

The materials used in constructing transdermal patch packaging and especially the patch contact package interior surface layer should resist migration of chemicals between the patch and the package materials. Such migration of the drug or patch components from the patch to the package structure is referred to as "scalping". Many commercial transdermal patches may include levels of chemicals or drugs that are several times higher than the intended, released dose. For example, a commercial, transdermal nicotine patch that can release a dose of 21 mg of nicotine may contain several times more nicotine such as, for example, 100 mg, 110 mg, 120 mg, 130 mg, 140 mg, or even 150 mg of nicotine. A common material employed for transdermal patch package interior surface layers that prevents scalping is polyacrylonitrile which is often sold under the BAREX trademark by Ineos AG. While BAREX has superb anti-scalping properties it is very expensive, has poor tear properties that make pouch opening difficult, and has limited availability which creates supply chain risk. Other polymers used in transdermal patch packaging as a surface contact layer include polyester (polyethylene terephthalate (PET)). PET suffers from the disadvantage of being less resistant to scalping of certain chemicals than desired and its tear properties are also less than desired. Accordingly, there is a need for a more cost efficient packaging material for containing articles that collect or administer a physiologically active substance such as transdermal drug delivery patches.

SUMMARY

Multilayered films for packaging comprising copolyester-based product-contacting layers resist migration of chemicals, such as pharmacological active agents or excipients, between the product and the film. Thus, the films are anti-scalping films.

In an aspect, provided is a multilayer flexible film for packaging a transdermal patch product comprising a pharmaceutical active agent, the film comprising: a product-contacting sealing layer comprising a co-polyester having a surface energy of at least 50 dyne/$cm^2$; and one or more layers above the product-contacting sealing layer.

The product-contacting sealing layer may comprise a thickness in the range of about 0.1 mil (2.5 micrometer) to about 2 mil (50.8 micrometer).

The co-polyester may have a glass transition temperature (Tg) of 70° C. or greater. The co-polyester may be a copolymer of polyethylene terephthalate material having glass transition temperature (Tg) of about 125° C.

The multilayer flexible film may further comprise: an exterior protective layer, and an oxygen barrier layer located between the exterior protective layer and the product-contacting sealing layer. The oxygen barrier layer may have an oxygen transmission rate of less than less than 0.155 $cm^3/m^2$ per 24 hours at 1 atmosphere and 23° C.; and the exterior protective layer comprises a polymer selected from the group consisting of paper, oriented polyester, amorphous polyester, polyamide, polyolefin, nylon, polypropylene, or copolymers, blends or derivatives thereof.

The multilayer flexible film may further comprise: an exterior protective layer comprising a polymer selected from the group consisting of paper, oriented polyester, amorphous polyester, polyamide, polyolefin, nylon, polypropylene, or copolymers, blends or derivatives thereof; inner layers located between the exterior protective layer and the product-contacting sealing layer, the inner layers comprising: a tie layer adjacent to exterior protective layer; a first inner layer adjacent to the tie layer; an oxygen barrier layer adjacent to the first inner layer having an oxygen transmission rate of less than less than 0.155 $cm^3/m^2$ per 24 hours at 1 atmosphere and 23° C.; an adhesive layer adjacent to the oxygen barrier layer; a second inner layer adjacent to the adhesive layer and the product-contacting layer. The exterior protective layer may comprise oriented polyester, the first inner layer comprises a LDPE-ethylene acrylic acid copolymer, the second inner layer comprises an amorphous polyester, and the oxygen barrier layer comprises foil.

The product-contacting sealing layer may exhibit an uptake of less than 10% by weight of the pharmaceutical active agent in the transdermal patch product after 1 week of aging at 100° F. (38° C.) and 20% relative humidity. The product-contacting sealing layer may exhibit no measurable uptake of the pharmaceutical active agent after 1 week of aging at 100° F. (38° C.) and 20% relative humidity.

A pressure-sensitive adhesive of the transdermal patch product may comprise one or more of: a silicone-based adhesive, an acrylate-based adhesive, and a polyisobutylene (PIB)-based adhesive.

An average adhesion force to peel the transdermal patch product from the product-contacting sealing layer after 60 minutes at 40° C. and 20% relative humidity at a peel rate of 12 inches/min (30.48 cm/min) using a 180° pull angle and a total pull length of 1.5 inches (3.81 cm) may be less than 100 g/inch (39.37 g/l cm). The average adhesion force may be about 7±0.5 g/inch (2.76±0.20 g/cm).

The pharmaceutical active agent may be nicotine.

In another aspect, a packaged transdermal patch product comprising a pharmaceutical active agent comprises: a flexible pouch comprising a film according to any embodiment of the disclosure; a transdermal patch sealed in the pouch. The flexible pouch may comprise: a first panel and a second panel sealed to one another at a perimeter seal defining a perimeter of a compartment of the pouch; one or more scores disposed on the first panel, the second panel, or both and extending from the perimeter seal. The packaged product may further comprise a tearing aid that intersects with the one or more scores. The transdermal patch may be a nicotine patch.

Another aspect is a method of making a packaged transdermal patch product comprising a pharmaceutical active agent comprising: forming a pouch from a film according to any embodiment of the disclosure; and sealing a transdermal patch in the pouch.

An aspect is a method of delivering a transdermal patch comprising: obtaining the packaged product according to any embodiment of the disclosure; and opening the pouch. An average adhesion force to peel the transdermal patch from the product-contacting sealing layer after 60 minutes at 40° C. and 20% relative humidity at a peel rate of 12 inches/min (30.48 cm/min) using a 180° pull angle and a total pull length of 1.5 inches (30.48 cm/min) may be less than 100 g/inch (39.37 g/cm).

These and other aspects of the invention are described in the detailed description below. In no event should the above summary be construed as a limitation on the claimed subject matter.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. It will be understood, however, that the use of a number to refer to a component in a given figure is not intended to limit the component in another figure labeled with the same number.

DETAILED DESCRIPTION

Transdermal patches generally use one of three kinds of pressure-sensitive adhesives (PSAs): (i) silicone-based (ii) acrylate-based and (iii) PIB-based. PSA of a transdermal patch that moves to a position in contact with sealant layers of the patch package is a phenomena referred to as 'cold-flow'. The adhered PSA material creates an additional interface for direct-contact nicotine transfer from the patch to the sealant in addition to the transfer of nicotine vapors from package headspace into the sealant. The PSA used in some common commercially-available nicotine patches, for example, those that can release a dose of 21 mg, 14 mg or 7 mg of nicotine, is polyisobutylene (PIB)-based. PIB-based materials are highly paraffinic and non-polar in nature. It has been found that PIB-based materials are highly adherent to polyolefin-based sealant film such as CXB™ (cyclic olefin copolymer film). On the other hand, BAREX (acrylonitrile methyl acrylate copolymer), which is highly polar due to its nitrile groups (dipole moment=3.9, Hansen δ (polar)=9), does not adhere to PIB-based materials. Silicone-based and acrylate-based PSAs are relatively more polar in nature than PIB-based PSAs. There is a need to identify sealant candidates which would be non-adherent towards PSAs, specifically PIB-based PSAs.

Provided are multilayer flexible films for packaging a transdermal patch product comprising a pharmaceutical active agent. By selecting a co-polyester, disadvantages with respect to polyester (polyethylene terephthalate (PET) and cyclic olefin copolymer (COC) films are addressed while maintaining or exceeding properties of BAREX-based films. That is, co-polyester materials having a surface energy of at least 50 dyne/cm$^2$ provide unexpected benefits of minimal to no uptake of the pharmaceutical active agent and excellent resistance to adhesives utilized in the products such as transdermal patches.

A "layer" as used herein refers to a structure of a single polymer-type or a blend of polymers.

An "exterior protective layer" as used herein refers to the portion of the package that is located outermost of all the layers and is subject to handling.

A "product-contacting sealing layer" is the innermost layer, one that seals to itself to form a hermetic seal. The sealing layer comprises a thermoplastic polymer or polymer mixture that softens when exposed to heat and returns to its original condition when cooled to room temperature.

As used herein, the term "polymer" refers to the product of a polymerization reaction, and is inclusive of homopolymers, copolymers, terpolymers, etc. In general, the layers of a film can consist essentially of a single polymer, or can have still additional polymers together therewith, i.e., blended therewith.

As used herein, the term "copolymer" refers to polymers formed by the polymerization of reaction of at least two different monomers.

As used herein, the term "polyester" refers to homopolymers or copolymers having an ester linkage between monomer units which may be formed, for example, by condensation polymerization reactions between a dicarboxylic acid and a glycol. The ester can be represented by the general formula: $[R—C(O)O—R']_n$, Where R and R'=alkyl group and may be generally formed from the polymerization of dicarboxylic acid and diol monomers or monomers containing both carboxylic acid and hydroxy moieties.

As used herein, "EVOH" refers to ethylene vinyl alcohol copolymer. EVOH is otherwise known as saponified or hydrolyzed ethylene vinyl acetate copolymer, and refers to a vinyl alcohol copolymer having an ethylene comonomer. EVOH is prepared by the hydrolysis (or saponification) of an ethylene-vinyl acetate copolymer. The degree of hydrolysis is preferably from about 50 to 100 mole percent, more preferably from about 85 to 100 mole percent, and most preferably at least 97%. It is well known that to be a highly effective oxygen barrier, the hydrolysis-saponification must be nearly complete, i.e., to the extent of at least 97%. EVOH is commercially available in resin form with various percentages of ethylene and there is a direct relationship between ethylene content and melting point. For example, EVOH having a melting point of about 175° C. or lower is characteristic of EVOH materials having an ethylene content of about 38 mole percent or higher. EVOH having an ethylene content of 38 mole percent has a melting point of about 175° C. With increasing ethylene content, the melting point is lowered. A melting point of about 158° C. corresponds to an ethylene content of 48 mole percent. EVOH copolymers having lower or higher ethylene contents may also be employed. It is expected that processability and orientation would be facilitated at higher contents; however, gas permeabilities, particularly with respect to oxygen, may become undesirably high for certain packaging applications which are sensitive to microbial growth in the presence of oxygen. Conversely, lower contents may have lower gas permeabilities, but processability and orientation may be more difficult. Preferably, ethylene/vinyl alcohol copolymers comprise from about 27-38 mole % ethylene, or even 27-29 mole % ethylene.

The term "adhesive layer," or "adhesive coating," refers to a material placed on one or more layers, partially or entirely, to promote the adhesion of that layer to another surface. Preferably, adhesive layers or coatings are positioned between two layers of a multilayer film to maintain the two layers in position relative to each other and prevent undesirable delamination. Unless otherwise indicated, an adhesive layer or coating can have any suitable composition that provides a desired level of adhesion with the one or more surfaces in contact with the adhesive layer material. Optionally, an adhesive layer or coating placed between a first layer and a second layer in a multilayer film may comprise components of both the first layer and the second layer to promote simultaneous adhesion of the adhesive layer to both the first layer and the second layer to opposite sides of the adhesive layer.

A "sidewall" is a discrete piece of polymer film or multi-layer laminate that is sealed to itself or another sidewall by, for example, welding, or by an adhesive, to form a pouch.

Sidewall Materials

A sidewall is typically formed from a multi-layered laminate. In general terms, there is at least an exterior layer and an inner layer. In specific terms, there may be an exterior protective layer, an optional inner or barrier layer, and a product-contacting sealing layer.

Product-Contacting Sealing Layer

The product-contacting sealing layer comprises a co-polyester having a surface energy of at least 50 dyne/cm$^2$ or at least 60 dyne/cm$^2$. The glass transition temperature (Tg) may be about 70° C. or greater. The range of Tg may be about 70° C. to about 150° C., or about 100° C. to about 150° C., or about 105° C. to about 150° C., or about 110'C to about 150° C. A non-limiting example of a co-polyester material is a co-polyester having a Tg of about 125° C. The product-contacting sealing layer may comprise a thickness in the range of about 0.1 mil (2.5 micrometer) to about 2 mil (50.8 micrometer), about 0.5 mil (12.7 micrometer) to about 1.5 mil (38.1 micrometer), or about 0.75 mil (19.1 micrometer) to about 1.25 mil (31.8 micrometer). In a detailed embodiment, the product-contacting sealing layer has a thickness of about 1 mil (25 micrometer).

Films and packaging described herein may include one or more additional optional layers, such as an exterior protective layer, one or more barrier layers, one or more intermediate layers, which may include one or more tie layers.

Exterior Protective Layer

The films described herein may include an exterior protective layer. Since it is seen by the user/consumer, in both monolayer and multilayer embodiments, the exterior surface of the film preferably has desirable optical properties and may preferably have high gloss. Also, it preferably withstands contact with sharp objects and provides abrasion resistance, and for these reasons it is often termed the abuse resistant or protective layer. This exterior protective layer may or may not also be used as a heat sealable layer. As the exterior surface layer of the film, this layer most often is also the exterior layer of any package, bag, pouch or other container made from a film described herein, and is therefore subject to handling and abuse e.g. from equipment during packaging, and from rubbing against other packages and shipping containers and storage shelves during transport and storage. This contact causes abrasive forces, stresses and pressures which may abrade away the film causing defects to printing, diminished optical characteristics or even punctures or breaches in the integrity of the package. Therefore the exterior surface layer is typically made from materials chosen to be resistant to abrasive and puncture forces and other stresses and abuse which the packaging may encounter during use. The exterior surface layer should be easy to machine (i.e. be easy to feed through and be manipulated by machines e.g. for conveying, packaging, printing or as part of the film or bag manufacturing process). Suitable stiffness, flexibility, flex crack resistance, modulus, tensile strength, coefficient of friction, printability, and optical properties are also frequently designed into exterior layers by suitable choice of materials. This layer may also be chosen to have characteristics suitable for creating desired heat seals which may be heat resistance to burn through e.g. by impulse sealers or may be used as a heat sealing surface in certain package embodiments e.g. using overlap seals. The exterior layer may be tough to impart resistance to opening by children e.g. preventing the package from being opened by a child's bite. A preferred exterior child resistant layer comprises a polyester film, preferably polyester terephthalate, which is preferably at least 0.9 mil (22.9 micrometer) in thickness. Suitable exterior surface layers may comprise: paper, oriented polyester, amorphous polyester, polyamide, polyolefin, cast or oriented nylon, polypropylene, or copolymers, or blends thereof. Oriented films of this or any other layer may be either uni-axially or bi-axially oriented. The exterior layer thickness is typically about 0.5 (12.7 micrometer) to about 2.0 mil (50.8 micrometer). Thinner layers may be less effective for abuse resistance, however thicker layers, though more expensive, may advantageously be used to produce films having unique highly desirable puncture resistance and/or abuse resistance properties.

Barrier Layer

If included, a barrier layer preferably functions both as a gas barrier layer, and as a moisture barrier layer, although these functions may be provided by separate layers. A gas barrier layer is preferably an oxygen barrier layer, and is preferably a core layer positioned between and protected by other layers. For example, an oxygen barrier layer can be in contact with the exterior layer and an intermediate layer. Further, an adhesive layer may be sandwiched between the oxygen barrier layer and the exterior layer.

An oxygen barrier is preferably selected to provide an oxygen permeability sufficiently diminished to protect the packaged article from undesirable deterioration or oxidative processes. For example, a film may comprise an oxygen barrier having an oxygen permeability that is low enough to prevent oxidation of oxygen sensitive articles and substances to be packaged in the film e.g. oxygen sensitive articles such as transdermal patches e.g. nicotine or fentanyl patches or oxygen sensitive collection samples such as blood which may be collected e.g. in a microcassette device. Preferably a multilayer packaging film in accordance with the present invention will have an oxygen barrier of less than or equal to 155 cm$^3$/m$^2$ per 24 hours at 1 atmosphere and 23° C., more preferably less than 0.016 cm$^3$/m$^2$ per 24 hours at 1 atmosphere. To protect oxygen sensitive articles from deterioration from oxygen contact over time the films according to the present invention will have a preferred oxygen transmission rate (O$_2$TR) of less than 15.5, preferably less than 1.55, more preferably less than 0.155, and most preferably less than 0.0155 cm$^3$/m$^2$ at 24 hours at Room Temperature (RT) (~23° C.) and 1 atmosphere.

A moisture barrier is preferably selected to provide a moisture permeability sufficiently dimensioned to protect the packaged article from undesirable deterioration. For example, a film may comprise a water barrier having a moisture permeability that is low enough to prevent deleterious effects upon packaged articles such as transdermal drug patches or other moisture sensitive products. A preferred film according to various embodiments will have a water or moisture transmission rate (WVTR) of less than 0.155 g/m$^2$ per 24 hours at Room Temperature (RT) (23° C.) and 1 atmosphere. In some embodiments, a film has a WVTR of less than 0.155 g/m$^2$ per 24 hours at Room Temperature (RT) (23° C.) and 1 atmosphere, or less than 0.0155 g/m$^2$ per 24 hours at Room Temperature (RT) (23° C.) and 1 atmosphere.

A barrier layer can comprise any suitable material. An oxygen barrier layer can comprise EVOH, polyvinylidene chloride, polyamide, polyester, polyalkylene carbonate, polyacrylonitrile, nanocomposite, a metallized film such as aluminum vapor deposited on a polyolefin, etc., as known to those of skill in the art. Suitable moisture barrier layers include aluminum foil, PVDC, or polyolefins such as LDPE or LLDPE. It is desirable that the thickness of the barrier layer be selected to provide the desired combination of the performance properties sought e.g. with respect to oxygen permeability, and delamination resistance, and water barrier properties. Suitable thicknesses in multilayer films are less than 15%, e.g. from 3 to 13% of the total film thickness and preferably less than about 10% of the total thickness of the multilayer film. Greater thicknesses may be employed however oxygen barrier polymers tend to be relatively expensive and therefore it is expected that less costly resins will be used in other layers to impart desirable properties once a suitable thickness is used to achieve the desired gas barrier property for the film layer combination. For example, the thickness of a core oxygen barrier layer may advantageously be less than about 0.45 mil (11.43 micrometers) and greater than about 0.05 mil (1.27 micrometers), including 0.10 mil (2.54 micrometers), 0.20 mil (5.08 micrometers), 0.25 mil (6.35 micrometers), 0.30 mil (7.62 micrometers), 0.40 mil (10.16 micrometers), or 0.45 mil (11.43 micrometers) thick.

An oxygen barrier layer of a film may comprise a metal or metal oxide layer, or EVOH, although oxygen barrier layers comprising polyvinylidene chloride-vinyl chloride copolymer (PVDC or VDC-VC) or vinylidene chloride-methyl acrylate copolymer (VDC-MA) as well as blends thereof, can also be used. One suitable EVOH barrier material is a 44 mol % EVOH resin E151B sold by Eval Company of America, under the trade name EVAL® LC-E151B. Another example of an EVOH that may be acceptable can be purchased from Nippon Gohsei under the trade name Soamol® AT (44 mol % ethylene EVOH).

Any suitable metal or metal oxide layer can be used as a barrier layer. Examples of suitable metal and metal oxide layers include foils and deposited metals, such as aluminum foil, aluminum oxide, silicon oxide, metalized polyethylene terephthalate, and the like.

For packaging of oxygen sensitive articles such as drug patches, an oxygen (O$_2$) permeability of less than about 310 cm$^3$/m$^2$ for a 24 hour period at 1 atmosphere, 0% relative humidity and 23' C, and preferably less than 75 cm$^3$/m$^2$, more preferably less than 20 cm$^3$/m$^2$. The thickness of the core layer may be varied and beneficially may be from about 0.05 to about 0.60 mils (1.27-15.24 micrometers).

A bulk layer may be provided to provide additional functionality such as stiffness or heat sealability or to improve machinability, cost, flexibility, barrier properties, etc. Preferred bulk layers comprise one or more polyolefins such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification. The bulk layer may be of any suitable thickness from 0.1 mil (2.54 micrometers) to 7 mil (177.8 micrometers) or may even be omitted for use in certain applications, but is preferably present to improve especially stiffness/flexibility properties and heat sealability.

Intermediate Layer

An intermediate layer is any layer between the exterior layer and the sealing layer and may include oxygen barrier layers, tie layers or layers having functional attributes useful for the film structure or its intended uses. Intermediate layers may be used to improve, impart or otherwise modify a multitude of characteristics: e.g. printability for trap printed structures, machinability, tensile properties, flexibility, stiffness, modulus, designed delamination, easy opening features, tear properties, strength, elongation, optical, moisture barrier, oxygen or other gas barrier, radiation selection or barrier e.g. to ultraviolet wavelengths, etc. Suitable intermediate layers may include: adhesives, adhesive polymers, paper, oriented polyester, amorphous polyester, polyamide, polyolefin, nylon, polypropylene, or copolymers, or blends thereof Suitable polyolefins may include: polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification, LDPE, HDPE, LLDPE, EAO, ionomer, EMA, EAA, modified polyolefins e.g. anhydride grafted ethylene polymers, etc.

Tie Layer

A multilayer packaging film can include one or more adhesive layers, also known in the art as "tie layers," which can be selected to promote the adherence of adjacent layers to one another in a multilayer film and prevent undesirable delamination. A multifunctional layer is preferably formulated to aid in the adherence of one layer to another layer without the need of using separate adhesives by virtue of the compatibility of the materials in that layer to the first and second layers. Alternatively, the tie layers can serve as an intermediary to different adhesives that are compatible with different layers or can serve to aid in the adherence of one layer to another layer without the need of using a separate adhesive while serving as an intermediary between a different layer and an adhesive.

In some embodiments, adhesive layers comprise materials found in both the first and second layers that the adhesive layer adheres together. The adhesive layer may suitably be less than 10% and preferably between 2% and 10% of the overall thickness of the multilayer film. Adhesive resins are often more expensive than other polymers so the tie layer thickness is usually kept to a minimum consistent with the desired effect.

Fabrication

In general terms, to form the films disclosed herein, the following steps are used. A desired sidewall is formed by making a single layer or a multi-layered laminate. The sidewall comprises at least one layer that provides a product-contacting sealing layer comprising a co-polyester having a surface energy of at least 50 dyne/cm$^2$ or at least 60 dyne/cm². To form a multi-layered laminate, techniques known in the art may be used. Preferably, the process produces a flexible film. Examples of such processes include cast or blown film processes. In general terms, there is at least an exterior layer and an inner layer. In specific terms, there may be an exterior layer, an optional inner or barrier layer, and the product-contacting sealing layer.

Thus, the sidewall is formed by extruding at least a first polymer resin corresponding to the co-polyester having a surface energy of at least 50 dyne/cm² through a die. For multi-layers, multiple resins or prepared films or foils are used and attached to each other. An edge seal is formed by affixing, for example, heat sealing, the edges of the sidewall.

Anti-Scalping

Whether a product-contacting layer of a film performs effectively as an anti-scalping layer can be a subjective determination, with differing amounts of migration of a pharmaceutical active agent into a layer of a film being considered acceptable depending on, among other things, the active agent, the amount that the active agent migrates into layers of other films, and the like.

For purposes of the present application, a product contacting layer of a film is considered to serve as an effective anti-scalping layer if (i) a lower amount of the active agent migrates into the product contacting layer of the film (the test film) than migrates into a substantially similar film having a polyester, such as PET, product-contacting layer (the reference film) when a product containing the pharmaceutical active agent is positioned relative to the test and reference films such that the pharmaceutical active agent is in direct contact with the product contacting layers of the test and reference films; or (ii) an amount of the active agent migrates into the product contacting layer of the film (the test film) is not more than 15% greater than migrates into a substantially similar film having a BAREX product contacting layer (the reference film) when a product containing the pharmaceutical active agent is positioned relative to the test and reference films such that the pharmaceutical active agent is in direct contact with the product contacting layers of the test and reference films. Preferably, the product is sealed in a cavity formed, at least in part, by the test film and the product is sealed in a cavity formed, at least in part, by the reference film. The sealed product can be stored under identical conditions prior to testing to determine whether less active agent has migrated into the product contacting layer of the test film than the reference film. The storage conditions may be accelerated storage conditions as described above.

Any suitable technique may be employed to determine whether less active agent has migrated into the product contacting layer of the test film than the reference film. For example, Raman spectroscopy or gas chromatography, can be used.

Before describing several exemplary embodiments of the invention, it is to be understood that the invention is not limited to the details of construction or process steps set forth in the following description. The invention is capable of other embodiments and of being practiced or being carried out in various ways.

Figure 1:
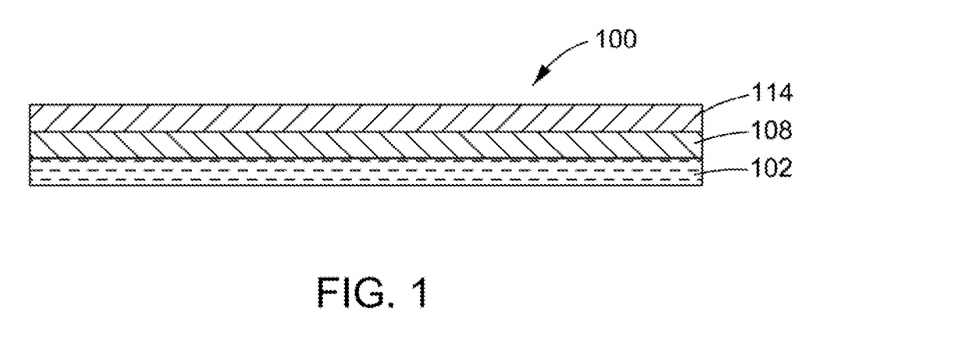
FIG. 1 is a schematic drawing of a cross-section of a multilayer film in accordance with embodiments presented herein.

Turning to the figures, FIG. 1 is a schematic drawing of a cross-section of an embodiment of a multilayer film 100. In the depicted embodiment, the film 100 includes three layers. On one surface is a product-contacting layer 102, which comprises a co-polyester copolymer, e.g., coPET having a dyne value of 50 dyne/cm² or greater. Adjacent and in contact with the product-contacting layer 102 is an oxygen barrier layer 108. Adjacent and in contact with the oxygen barrier layer 108 is an exterior protective layer 114.

Figure 2:
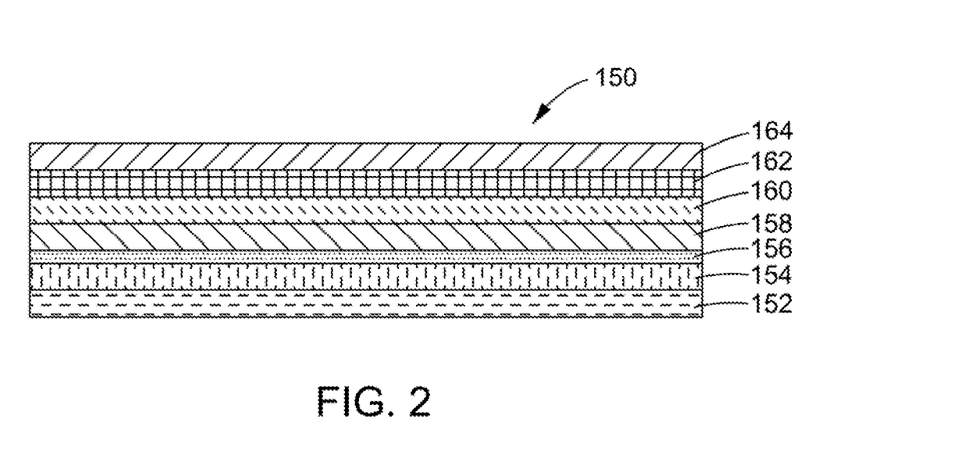
FIG. 2 is a schematic drawing of a cross-section of a multilayer film in accordance with embodiments presented herein.

Referring now to FIG. 2, a schematic drawing of a cross-section of an embodiment of a multilayer film 150 is shown. In the depicted embodiment, the film 150 includes seven layers. On one surface is a product-contacting layer 152, which comprises a co-polyester copolymer, e.g., coPET having a dyne value of 50 dyne/cm² or greater. Adjacent and in contact with the product-contacting layer 152 is a first intermediate layer 154 comprising amorphous PET. Adjacent and in contact with the first intermediate layer is an adhesive layer 156. Adjacent and in contact with the adhesive layer 156 is an oxygen barrier layer 158. The oxygen barrier layer can be a metal foil or deposited metal or metal oxide such as aluminum oxide, silicon oxide, metalized PET, or the like. Adjacent and in contact with the oxygen barrier layer 158 is a bulk layer 160, such as a layer that comprises a polyolefin such as polyethylene. Adjacent the bulk layer 160, in some embodiments, is a tie or adhesive layer 162. Adjacent and in contact with the tie or adhesive layer 162 is an exterior protective layer 164, which may be oriented PET. The bulk layer 160 and tie/adhesive layer 162, in some embodiments, can be coextruded with the exterior protective layer 164.

In some embodiments, a single roll web of pouch film can be placed on a packaging machine and folded together and heat sealed and severed to form heat sealed pouches. Two side sealed pouches with a folded third side can be used to package an article by a manufacturer or packager who places a product in the pouch, and completes the final seal to produce a hermetically sealed package containing for example: a transdermal drug delivery patch; an oral dissolvable thin strip containing a drug, flavorant, antimicrobial agent, odorant, and/or microbiologically active ingredient or combination thereof; or an article for collecting or administering a physiologically active substance.

Figure 3:
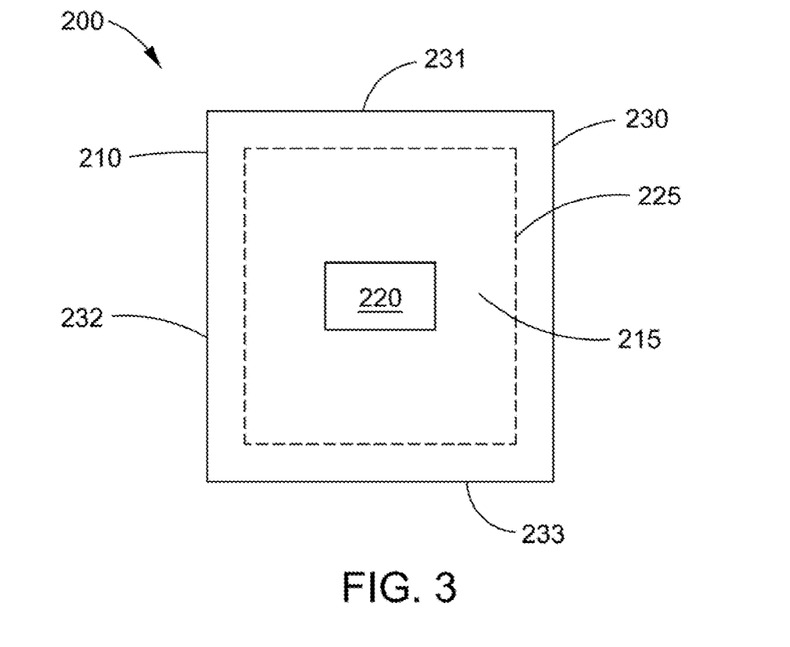
FIG. 3 is a schematic drawing of a packaged product in accordance with embodiments presented herein.

Referring now to FIG. 3, a schematic drawing of a packaged product 200 is shown. The packaged product includes a product 220, such as a pharmaceutical product, sealed within an interior 215 of the package that includes any film 210 of the disclosure. The product 220 is in contact with a product-contacting layer (not numbered) of the film 210. In some embodiments, the package consists essentially of the film 210. The film 210 forms the interior 215 of the package, which is defined by heat seal 225 that is formed along each edge 230, 231, 232, and 233 of the package. In the depicted embodiment, the dashed lines indicated the sealed portion of the package that defines sealed interior 215.

Figure 4:
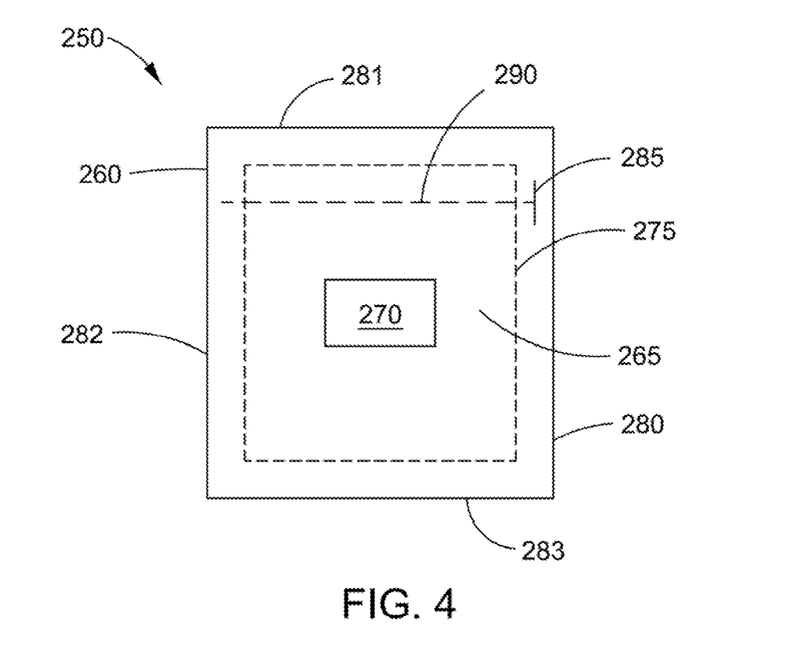
FIG. 4 is a schematic drawing of a packaged product in accordance with embodiments presented herein.

In FIG. 4, a schematic drawing of a packaged product 250 is shown. The packaged product includes a product 270, such as a pharmaceutical product, sealed within an interior 265 of the package that includes any film 260 of the disclosure. The product 270 is in contact with a product-contacting layer (not numbered) of the film 260. In some embodiments, the package consists essentially of the film 260. The film 260 forms the interior 265 of the package, which is defined by heat seal 275 that is formed along each edge 280, 281, 282, and 283 of the package. In the depicted embodiment, the dashed lines indicate the sealed portion of the package that defines sealed interior 265. A score 290 traverses the package from an offset of each edge 280 and 282. A tearing aid 285 is substantially perpendicular to score 290.

EXAMPLES

Example 1

Transdermal packaging film was made using tandem lamination having the structure set forth in Table 1.

TABLE 1

| Layer | Composition | Thickness (micrometers) |
|---|---|---|
| 1 | Oriented polyethylene terephthalate (OPET) | 23 |
| 2 | Tie layer | |
| 3 | Blend of low density polyethylene (LDPE) and ethylene acrylic acid (EAA) copolymer | |
| 4 | Aluminum foil | 9 |
| 5 | Adhesive | |
| 6 | Amorphous polyethylene terephthalate (APET) | 17 |
| 7 | Polyethylene terephthalate copolymer (CoPET) | 8 |

This structure is abbreviated as: OPET/tie/LDPE-EAA/Foil/Adh/APET/coPET. The co-PET material was a co-polyester having a Tg of about 125° C.

Example 2

For evaluating heat sealing performance (seal-to-self), 1 inch (2.54 cm) wide strip samples of the film of Example 1 were cut from the film and sealed under conditions of varying sealing temperatures (350-450° F.) (177-232° C.), sealing pressure of 30 pounds/inch$^2$ (206.8 KPa) and a dwell time of 0.5 second. Three replicates were evaluated for each sample type. The seal strength for the samples was evaluated using an Instron. Table 2 shows the seal strength data for the different sample types and indicates that significantly high seal strengths can be obtained at temperatures >380° F. (193° C.).

TABLE 2

Peak Seal Strength

| Temperature | CoPET (g/inch) | CoPET (N/mm) |
|---|---|---|
| 350° F. (177° C.) | 1023.00 | 0.39 |
| 370° F. (188° C.) | 2295.67 | 0.88 |
| 390° F. (199° C.) | 3801.33 | 1.47 |
| 400° F. (204° C.) | 3915.33 | 1.51 |
| 410° F. (210° C.) | 3932.33 | 1.52 |
| 430° F. (221° C.) | 4101.33 | 1.58 |
| 450° F. (232° C.) | 4502.67 | 1.74 |

Example 3

Figure 5:
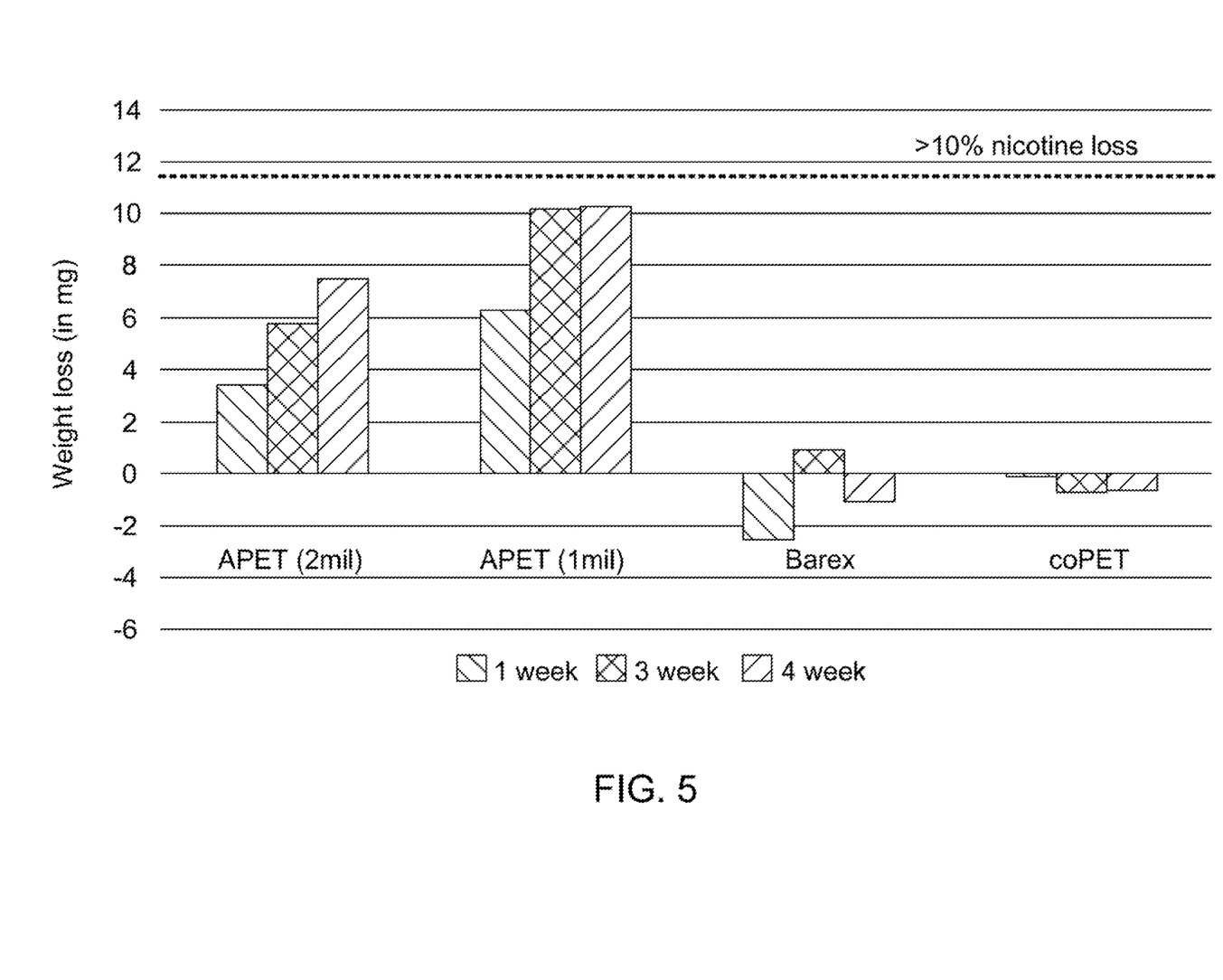
FIG. 5 is a graph of weight loss over time of packaged, commercially-available, nicotine transdermal patches that deliver doses of 21 mg of nicotine.

Nicotine Uptake. 3.5×3 inch (8.9 cm×7.6 cm) pouches were made from the film of Example 1. Comparative pouches were also made from films analogous to Example 1 with different product-contacting layers: BAREX and APET of two thicknesses. Commercially-available nicotine transdermal patches with polyisobutylene-based pressure sensitive adhesive, providing a dose of 21 mg of nicotine were packaged inside the pouches. The pouches were then kept under accelerated aging conditions (100° F. (38° C.), 20% Relative Humidity). The weights of the patches were recorded beforehand and the weight-loss was quantified over several weeks. Table 3 and FIG. 5 summarize the results and indicate that coPET has low nicotine uptake comparable to BAREX and that the comparative APET films showed significant weight loss of the patches. In FIG. 5, weight loss is shown as positive values; weight gain is shown as negative values.

TABLE 3

Patch Weight Loss - Average (in mg)

| Sample ID | 1 week | 3 weeks | 4 weeks |
|---|---|---|---|
| APET (2 mil) Comparative | 3.47 | 5.8 | 7.5 |
| APET (1 mil) Comparative | 6.33 | 10.23 | 10.33 |
| BAREX (2 mil) Prior art | −2.6 | 0.93 | −1.17 |
| coPET (1 mil) Inventive | −0.13 | −0.77 | −0.67 |

Example 4

Monolayer polymer sheets for each product-contacting layer type of Example 3 were cut into 1 inch by ⅜ inch (2.54 cm×0.95 cm) strips. The strips were then clipped individually on a wire, and hung in a jar filled with 50 ml nicotine at the bottom. The strip samples were exposed to nicotine vapor for up to 6 weeks under accelerated aging condition (100° F. (38° C.), 20% RH). After the allotted time, the strip samples were placed in 1.5 ml of isopropanol and placed on a shaker table overnight to facilitate nicotine extraction from the sealant. Finally, the pouch extracts are analyzed by gas chromatography and the amount of eluted nicotine was calculated for each strip. Table 4 indicates that the nicotine uptake property (no measurable amount) of coPET was as good as BAREX.

TABLE 4

Nicotine Uptake - Average (in micrograms)

| Sample ID | 1 week | 3 weeks | 4 weeks |
|---|---|---|---|
| APET (2 mil) | 66.95 | 86.61 | 233.33 |
| BAREX (2 mil) Prior art | 0 | 0 | 0 |
| coPET (2 mil) Inventive | 0 | 0 | 0 |

Example 5

Tests were conducted to evaluate the adhesive affinity of the polyisobutylene-based pressure sensitive adhesive (PSA) used in commercial transdermal nicotine patches towards different sealant material. 4"×1" (10.16 cm×2.54 cm) strips of film analogous to those of Example 1 presenting different sealant surfaces (APET, copolyester, BAREX, cyclic olefin copolymer (e.g., CXB™)) were created. Commercially-available nicotine transdermal patches with polyisobutylene-based pressure sensitive adhesive, providing a dose of 21 mg of nicotine were applied to the sealant surfaces under a weight of 1.4 kg for 30 seconds with the pressure-sensitive adhesive of the patches in direct contact with the sealant of the transdermal film. The strips of transdermal film (with adhered nicotine patch) were incubated at 40° C. and 20% Relative Humidity for 60 minutes. An Instron machine was used to measure the force needed to peel the sealant apart from the adhered nicotine patch at a peel rate of 12 inches/min (30.48 cm/min) using a 180° pull angle and a total pull length of 1.5 inches (3.81 cm). 3-4 replicates were evaluated for different films. Table 5 summarizes the results for the tests in the form of peak force and average force of adhesion for all the samples.

TABLE 5

| Sample ID | Peak Adhesion Force | Average Adhesion Force |
|---|---|---|
| COC (Cyclic Olefin Copolymer) (2 mil sealant thickness) Prior art | 2291 ± 360 g/inch 0.88 ± 0.14 N/mm | 1391 ± 103 g/inch 0.53 ± 0.04 N/mm |
| APET (2 mil sealant thickness) Comparative | 1667 ± 136 g/inch 0.64 ± 0.05 N/mm | 1352 ± 43 g/inch 0.52 ± 0.01 N/mm |
| BAREX (2 mil sealant thickness) Prior art | 97 ± 33 g/inch 0.03 ± 0.01 N/mm | 25 ± 1 g/inch 0.01 + 0.0003 N/mm |
| coPET (1 mil sealant thickness) inventive | 115 ± 47 g/inch 0.044 ± 0.007 N/mm | 7 ± 0.5 g/inch 0.003 ± 0.0002 N/mm |

The results indicate that the coPET is highly resistant to adhesion towards the PIB-based PSA used in the commercial 21 mg nicotine transdermal patches and its adhesion values are similar to BAREX.

Example 6

Films analogous to those of Example 1 presenting different sealant surfaces (APET, copolyester, BAREX, cyclic olefin copolymer (e.g., CXB™)) were created.

Contact angles were measured according to ASTM 05946 ("Standard Test Method for Corona-Treated Polymer Films Using Water Contact Angle Measurements") with respect to varying solvents as provided in Table 6. Contact angle was measured using captured digital images and image analysis techniques of 2-4 microliter drops on the film surface as described in D5496. The same technique was used for di-iodomethane and formamide. Calculation of polar and dispersive components was done either by the harmonic approach of Wu or the geometric approach of Owens-Wendt. The software would normally use the method of Wu unless negative roots were obtained and then it would automatically switch to the Owens-Wendt approach. Acid-base components were calculated using the Van Oss-Chaudhury-Good approach.

TABLE 6

| Sample ID | Water | Di-iodomethane | Formamide |
|---|---|---|---|
| CXB™ COC film (Cyclic Olefin Copolymer) (2 mil sealant thickness) Prior art | 92.5° | 44.1° | 78.6° |
| APET (2 mil sealant thickness) Comparative | 67.9° | 22.4° | 55.4° |
| BAREX (2 mil sealant thickness) Prior art | 62.6° | 32.8° | 42.5° |
| coPET (1 mil sealant thickness) Inventive | 64.2° | 18.9° | 51.1° |

Although not as polar as BAREX (Hansen δ (polar)=9), coPET-based resins (Hansen δ (polar)=5-7) are more polar than CXB™ (Hansen δ (polar)=3). The contact angles of different solvents with coPET-based sealant are similar to BAREX and therefore coPET is similarly non-repellent towards a PIB-based PSA.

Surface energies were also calculated as provided in Table 7.

TABLE 7

| Sample ID | Total Surface Energy mJ/m$^2$ | Dispersive Component mJ/m$^2$ | Acid/Base Component mJ/m$^2$ |
|---|---|---|---|
| CXB™ COC film (Cyclic Olefin Copolymer) 2 mil sealant thickness) Prior art | 43.0 | 37.5 | 5.5 |
| APET (2 mil sealant thickness) Comparative | 52.1 | 47.0 | 5.0 |
| BAREX (2 mil sealant thickness) Prior art | 47.2 | 43.2 | 4.2 |
| coPET (1 mil sealant thickness) inventive | 52.0 | 48.1 | 3.9 |

Dyne measurements were also obtained by pressing a dyne test pen against the surface of the substrate and applying the dyne solution in a line across the substrate surface. The dyne solution is observed for two seconds. If beading does not occur at the center of the line within two seconds, the next highest dyne level pen should be used and testing should be performed in the same manner. Once beading occurs within two seconds at the center of the line, that level of dyne solution is reported as the dyne measurement and the measurement is complete. The measurement is completed at standard room temperature and humidity. Results are provided in Table 8.

TABLE 8

| Sample ID | Surface Energy dyne/cm$^2$ |
|---|---|
| CXB™ COC film (Cyclic Olefin Copolymer) (2 mil sealant thickness) Prior art | 32 |
| APET (2 mil sealant thickness) Comparative | 46 |
| BAREX (2 mil sealant thickness) Prior art | >60 |
| coPET (1 mil sealant thickness) Inventive | 60 |

Tables 7 and 8 indicate that the coPET surface has high surface energy similar to BAREX and dissimilar to CXB™ COC or APET. A high surface energy generally indicates hydrophilicity and an increased ability of 'polar' adhesives or materials to wet out the surface. PIB-based PSA is highly non-polar and paraffinic in nature, it does not adhere well to polar surfaces. This is consistent with Table 5, where the adhesion force of coPET the PSA was similar to BAREX and much lower than CXB™ COC or APET.

Example 7

Various co-PET materials of varying glass transition temperature (Tg) were tested for nicotine uptake in accordance with Example 4. All samples were 5 mil thick. The results are provided in Table 9.

TABLE 9

| Sample | Tg (° C.) | Nicotine Uptake (in mg) | | |
|---|---|---|---|---|
| | | 1 week | 2 week | 4 week |
| A[(1)] | 125 | 0.000 | 0.000 | 0.000 |
| B | 118 | 0.000 | 0.000 | 0.000 |
| C | 110 | 0.000 | 0.000 | 0.000 |
| D | 103 | 0.009 | 0.012 | 0.018 |
| E | 65 | 0.528 | 0.636 | 1.690 |

[(1)]Sample A was used in Example 1.

For certain applications, utilizing Tg of 70° C. or greater, or 100° C. or greater, or 103° C. or greater, may provide acceptable properties. As indicated by Table 9, to ensure zero nicotine uptake, a Tg of 105° C. or greater or 110° C. or greater is preferred.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A multilayer flexible film for packaging a transdermal patch product comprising a pharmaceutical active agent, the film comprising:
a product-contacting sealing layer comprising a co-polyester having a surface energy of at least 50 dyne/$cm^2$; and
one or more layers above the product-contacting sealing layer.

2. The multilayer flexible film of claim 1, wherein the product-contacting sealing layer comprises a thickness in the range of about 0.1 mil (2.5 micrometer) to about 2 mil (50.8 micrometer).

3. The multilayer flexible film of claim 1, wherein the co-polyester has a glass transition temperature (Tg) of 70° C. or greater.

4. The multilayer flexible film of claim 1, wherein the co-polyester is a co-polyethylene terephthalate material having glass transition temperature (Tg) of about 125° C.

5. The multilayer flexible film of claim 1 further comprising: an exterior protective layer, and an oxygen barrier layer located between the exterior protective layer and the product-contacting sealing layer.

6. The multilayer flexible film of claim 5, wherein:
the oxygen barrier layer has an oxygen transmission rate of less than less than 0.155 $cm^3/m^2$ per 24 hours at 1 atmosphere and 23° C.; and
the exterior protective layer comprises a polymer selected from the group consisting of paper, oriented polyester, amorphous polyester, polyamide, polyolefin, nylon, polypropylene, or copolymers, blends or derivatives thereof.

7. The multilayer flexible film of claim 1 further comprising:
an exterior protective layer comprising a polymer selected from the group consisting of paper, oriented polyester, amorphous polyester, polyamide, polyolefin, nylon, polypropylene, or copolymers, blends or derivatives thereof;
inner layers located between the exterior protective layer and the product-contacting sealing layer, the inner layers comprising:
a tie layer adjacent to exterior protective layer;
a first inner layer adjacent to the tie layer;
an oxygen barrier layer adjacent to the first inner layer having an oxygen transmission rate of less than less than 0.155 $cm^3/m^2$ per 24 hours at 1 atmosphere and 23° C.;
an adhesive layer adjacent to the oxygen barrier layer;
a second inner layer adjacent to the adhesive layer and the product-contacting layer.

8. The multilayer flexible film of claim 7, wherein exterior protective layer comprises oriented polyester, the first inner layer comprises a LDPE-ethylene acrylic acid copolymer, the second inner layer comprises an amorphous polyester, and the oxygen barrier layer comprises foil.

9. The multilayer flexible film of claim 1, wherein the product-contacting sealing layer exhibits an uptake of less than 10% by weight of the pharmaceutical active agent in the transdermal patch product after 1 week of aging at 100° F. (38° C.) and 20% relative humidity.

10. The multilayer flexible film of claim 9, wherein the product-contacting sealing layer exhibits no measurable uptake of the pharmaceutical active agent after 1 week of aging at 100° F. (38° C.) and 20% relative humidity.

11. The multilayer flexible film of claim 1, wherein a pressure-sensitive adhesive of the transdermal patch product comprises one or more of: a silicone-based adhesive, an acrylate-based adhesive, and a polyisobutylene (PIB)-based adhesive.

12. The multilayer flexible film of claim 1, wherein an average adhesion force to peel the transdermal patch product from the product-contacting sealing layer after 60 minutes at 40° C. and 20% relative humidity at a peel rate of 12 inches/min (30.48 cm/min) using a 180° pull angle and a total pull length of 1.5 inches (3.81 cm) is less than 100 g/inch (39.37 g/cm).

13. The multilayer flexible film of claim 12, wherein the average adhesion force is about 7±0.5 g/inch (2.76±0.20 g/cm).

14. The multilayer flexible film of claim 1, wherein the pharmaceutical active agent is nicotine.

15. A packaged transdermal patch product comprising a pharmaceutical active agent comprising:
   a flexible pouch comprising a film according claim 1;
   a transdermal patch sealed in the pouch.

16. The packaged product of claim 15, wherein the flexible pouch comprises:
   a first panel and a second panel sealed to one another at a perimeter seal defining a perimeter of a compartment of the pouch;
   one or more scores disposed on the first panel, the second panel, or both and extending from the perimeter seal.

17. The packaged product of claim 16 further comprising a tearing aid that intersects with the one or more scores.

18. The packaged product of claim 15, wherein the transdermal patch is a nicotine patch.

19. A method of making a packaged transdermal patch product comprising a pharmaceutical active agent comprising:
   forming a pouch from a film according to claim 1; and
   sealing a transdermal patch in the pouch.

20. A method of delivering a transdermal patch comprising:
   obtaining the packaged product of claim 15; and opening the pouch.

* * * * *